United States Patent [19]

Plantema et al.

[11] Patent Number: 4,563,308

[45] Date of Patent: Jan. 7, 1986

[54] RECOVERY OF CAPROLACTAM FROM CAPROLACTAM-CONTAINING DISTILLATION RESIDUE

[75] Inventors: Otto G. Plantema, Nederweert-Eind; Arnold G. M. Jetten, Ulestraten; Nicolaas F. Haasen, Sittard, all of Netherlands

[73] Assignee: Stamicarbon B.V., Licensing Subsidiary of DSM, Geleen, Netherlands

[21] Appl. No.: 643,026

[22] Filed: Aug. 21, 1984

[30] Foreign Application Priority Data

Aug. 31, 1983 [NL] Netherlands ............... 8303028

[51] Int. Cl.$^4$ ............................................. C07D 201/04
[52] U.S. Cl. .............................................. 260/239.3 A
[58] Field of Search ................................. 260/239.3 A

[56] References Cited

U.S. PATENT DOCUMENTS 4,017,482 4/1977 Gath ..................... 260/293.3 A
4,257,950 3/1981 Horn ..................... 260/293.3 A
4,268,440 5/1981 Werther ................. 260/293.3 A

FOREIGN PATENT DOCUMENTS 0065168 11/1982 European Pat. Off. .

OTHER PUBLICATIONS

83 Chem. Abs. 98134 h (1975).

Primary Examiner—Paul R. Michl
Attorney, Agent, or Firm—Cushman, Darby & Cushman

[57] ABSTRACT

Process the recovering caprolactam from the residue remaining following the distillation, under reduced pressure, of impure caprolactam obtained by rearrangement of cyclohexanone oxime with sulphuric acid or oleum, by distilling the residue under reduced pressure whereby a caprolactam-containing distillate is obtained; hydrogenating the caprolactam containing distillate in an aqueous medium to obtain a hydrogenation product; and recovering caprolactam from the resulting hydrogenation product.

14 Claims, No Drawings

RECOVERY OF CAPROLACTAM FROM CAPROLACTAM-CONTAINING DISTILLATION RESIDUE

The invention relates to a process for recovering caprolactam from the residue remaining in the distillation, under reduced pressure, of impure caprolactam obtained by rearrangement of cyclohexanone oxime with sulphuric acid or oleum.

In order to obtain caprolactam pure enough for the polymerization to Nylon-6, impure caprolactam obtained in the rearrangement of cyclohexanone oxime is subjected to a number of purification processes. In a final step the caprolactam to be purified is subjected to distillation under reduced pressure, which distillation can be carried out very efficiently in the manner described in European patent application No. 0 065 168.

The quantity of caprolactam yet contained in the residue remaining in this distillation process is such that its recovery in a sufficiently pure state is highly worthwhile.

A process known in the art for recovering caprolactam from a caprolactam-containing distillation residue (see European patent specification No. 0 022 161, published on Nov. 10, 1982) comprises a distillation process in two steps and a treatment of the resulting distillate with a strong acid, upon which caprolactam can be extracted from the distillate thus treated. Owing to the treatment with strong acid, this known process is rather expensive.

The invention now provides a highly suitable process for working up caprolactam-containing residue, in which process a treatment with strong acid is not necessary and in which, moreover, one distillation step will suffice.

The process according to the invention for recovering caprolactam from the residue remaining in the distillation, under reduced pressure, of impure caprolactam obtained by rearrangement of cyclohexanone oxime with sulphuric acid or oleum is characterized in that the residue is subjected to distillation under reduced pressure, the caprolactam-containing distillate obtained in that process is hydrogenated in an aqueous medium and caprolactam is recovered from the resulting hydrogenation product.

In the process according to the invention high-boiling and low-boiling impurities are separated off by the distillation under reduced pressure and a distillate is obtained containing the caprolactam to be recovered, however with a purity which is yet insufficient. This distillation under reduced pressure can be carried out in distillation equipment known per se, for instance a column with sieve plates or packing and 5-25 theoretical plates. The chosen temperature and pressure in the column may vary, for instance a temperature of 115°-250° C. in the bottom and a pressure in the top amounting to 3-500 mbar. Very suitable is a temperature of 120°-200° C. in the bottom and a pressure in the top of 5-150 mbar. In large scale distillation preference is given to using a packed column. As packing various materials known in the art are suitable such as, for instance, Intalox metal packing (described in Chemical Engineering Progress of March 1979, pages 86-91), Sulzer packing type BX (see Chemie Ingenieur Technik, vol. 37, page 322, 1965) and Sulzer packing type Mellapak (see Chemical Engineering Progress of November 1977, pages 71-77).

The hydrogenation of the caprolactam-containing distillate in aqueous medium can be carried out according to processes known per se, using hydrogenation catalysts known per se such as, for instance, ruthenium on aluminium oxide, rhodium on aluminium oxide, platinum on carbon, palladium on carbon, Raney nickel and nickel on silicon oxide. Preference is given to using a nickel-containing catalyst. The chosen concentration of the caprolactam containing distillate in the aqueous medium may vary, for instance between 10 to 95% (wt). Preference is given to a chosen concentration of between 30 and 75% (wt). This hydrogenation can furthermore be carried out at different temperatures, for instance temperatures from 20°-160° C. Preference is given to applying a temperature between 70° and 120° C. The chosen hydrogen pressure, too, may vary, for instance between 1 and 100 bar. High efficiencies are obtained at hydrogen pressures between 2 and 20 bar.

The recovery of the caprolactam from the aqueous hydrogenation mixture can be effected in various ways, for instance by fractionated distillation or extraction with benzene or toluene. If so desired, this fractionated distillation or extraction can be carried out jointly with a suitable process of the working-up processes of the caprolactam obtained in the rearrangement of cyclohexanone oxime, in which the caprolactam-containing residue to be worked up according to the invention remains.

The invention will be further elucidated in the following examples.

EXAMPLE I

In a vacuum distillation device consisting of a rectification column with condenser and a falling film evaporator for heating the bottom liquid, lactam is recovered from distillation residue (purity 99% (wt)) which has been left in the cleaning of caprolactam by distillation in the manner described in European patent application No. 0 065 168. The falling film evaporator used is a Normag type 9318 S. In the rectification column (diameter 5 cm) 20 sieve plates (13 theoretical plates) are applied.

The distillation residue is fed in a quantity of 1642 grammes/hour to the rectification column, on the fifth sieve plate from the bottom. The pressure in the top of the rectification column in 13 mbar, the temperature in the bottom 178° C. and in the top 137° C. In the falling film evaporator a heating medium is used with a temperature of 213° C. With a total reflux, 1.5 grammes/hour vapour phase (low-boiling compounds) is carried off at the top of the column at a condenser temperature of 120° C.

Through a side stream drain on the tenth sieve plate from the bottom 1558 grammes/hour caprolactam is carried off at a temperature of 160° C. and a reflux ratio of 0.45. Of the bottom product obtained 82.5 grammes/hour is carried off.

The colour index of the caprolactam carried off via the side stream is 1° Hazen (50% (wt) aqueous caprolactam solution) and the permanganate number 1800.

Of the caprolactam obtained 100 grammes is mixed with 40 grammes water, upon which this mixture is stirred well for 1 hour at 80° C. in an autoclave having a capacity of 0.5 liter under a partial hydrogen pressure of 5 bar in the presence of 60 milligrammes Raney nickel. From the reaction mixture obtained the Raney nickel is filtered off. The permanganate number of the caprolactam in the resulting solution is 8000. After that the water is removed from this solution by distillation at atmospheric pressure. The remaining product is distilled at a pressure of 8 mbar and a temperature of 123° C. In a large scale process, this distillation can be combined, of course, with the purification by distillation as described in the said European patent application No. 0 065 168).

95 grammes caprolactam is obtained having a permanganate number of 12000.

EXAMPLE II

Example I is repeated, however with 130 milligrammes nickel on $SiO_2$ (35% (wt) nickel) instead of the Raney nickel. The result obtained equals that mentioned in example I.

EXAMPLE III

Example I is repeated, however with 10 milligramme ruthenium on $Al_2O_3$ (0.5% (wt) ruthenium) instead of Raney nickel. The permanganate numbr of the caprolactam obtained in the hydrogenation is 6000 and of the caprolactam recovered by the distillation from the hydrogenated product is 10,000.

We claim:

1. Process for recovering caprolactam from the residue remaining following the distillation, under reduced pressure, of impure caprolactam obtained by rearrangement of cyclohexanone oxime with sulphuric acid or oleum, comprising:
   distilling said residue under reduced pressure whereby a caprolactam-containing distillate is obtained;
   hydrogenating said caprolactam-containing distillate in an aqueous medium to obtain a hydrogenation product;
   and recovering caprolactam from the resulting hydrogenation product.

2. Process according to claim 1, wherein said distillation of said residue under reduced pressure is carried out in a packed column with 5-25 theoretical plates.

3. Process according to claim 2, wherein said column a bottom temperature between 120° and 200° C. is applied and a pressure in the top between 5 and 150 mbar.

4. Process according to claim 1, wherein said hydrogenation a nickel-containing catalyst is used.

5. Process according to claim 1, wherein said hydrogenation is carried out with a 30-75% (wt) concentration of said caprolactam-containing distillate in said aqueous medium.

6. Process according to claim 1, wherein said hydrogenation is carried out at a temperature of 70°-120° C.

7. Process according to claim 1, wherein said hydrogenation a partial hydrogen pressure of 2-20 bar is applied.

8. Process according to claim 1, wherein caprolactam is recovered from the resulting hydrogenation product by distillation.

9. Process for recovering caprolactam from the residue remaining following the distillation, under reduced pressure, of impure caprolactam obtained by rearrangement of cyclohexanone oxime with sulphuric acid or oleum, comprising:
   distilling said residue under reduced pressure in a packed column having 5-25 theoretical plates, said column having a bottom temperature of between 120° C. and 220° C., said column having a pressure in the top thereof of between 5 and 150 mbar, whereby a distillate containing caprolactam is obtained;
   hydrogenating said distillate containing caprolactam in an aqeuous medium in the presence of a catalyst containing nickel whereby a hydrogenation product is obtained; and
   recovering caprolactam from said hydrogenation product.

10. Process according to claim 9 wherein said hydrogenation is carried out with a 30-75 wt% concentration of said distillate containing caprolactam in said aqueous medium.

11. Process according to claim 9 wherein said hydrogenation is carried out a temperature of 70° C. to 120° C.

12. Process according to claim 10 wherein said hydrogenation a partial hydrogen pressure of 2 bar to 20 bar is applied.

13. Process according to claim 9 wherein said hydrogenation is conducted at a temperature of about 70° C. to about 120° C. at a partial hydrogen pressure of about 2 bar to about 20 bar with a 30-75 wt% concentration of said distillate containing caprolactam in said aqueous medium.

14. Process according to claim 10 wherein said caprolactam recovery from said hydrogenation product is by distillation.

* * * * *